United States Patent [19]

Cassar et al.

[11] 4,034,004
[45] July 5, 1977

[54] PROCESS FOR THE PREPARATION OF CARBOXYLIC ACIDS FROM ORGANIC HALIDES

[75] Inventors: Luigi Cassar; Marco Foá, both of Novara; Andrea Gardano, Trino Vercellese (Vercelli), all of Italy

[73] Assignee: Montedison Fibre S.p.A., Milan, Italy

[22] Filed: June 10, 1975

[21] Appl. No.: 585,756

[30] Foreign Application Priority Data

June 11, 1974 Italy .................................. 23849/74

[52] U.S. Cl. .......................... 260/515 R; 260/413; 260/515 A; 260/540
[51] Int. Cl.² ............................................ C07C 63/00
[58] Field of Search .............. 260/515 R, 532, 540, 260/413

[56] References Cited
UNITED STATES PATENTS

| | | | |
|---|---|---|---|
| 2,565,464 | 8/1951 | Tabet | 260/515 R |
| 3,437,676 | 4/1969 | Kutepow et al. | 260/515 R |
| 3,655,745 | 4/1972 | Fenton | 260/532 |
| 3,700,729 | 10/1972 | Fenton | 260/515 R |
| 3,708,529 | 1/1973 | Cassar et al. | 260/515 R |
| 3,769,326 | 10/1973 | Paulik et al. | 260/532 |
| 3,769,329 | 10/1973 | Paulik et al. | 260/532 |
| 3,919,272 | 11/1975 | Knifton | 260/413 |
| 3,968,133 | 7/1976 | Knifton | 260/532 |

OTHER PUBLICATIONS

Cassar et al., Chem. Abstracts, vol. 79, 125323(v) (1973).
Thompson et al., Chem Abstracts, vol. 77, 100238(s) (1972).

*Primary Examiner*—James O. Thomas, Jr.
*Assistant Examiner*—G. T. Breitenstein
*Attorney, Agent, or Firm*—Stevens, Davis, Miller & Mosher

[57] ABSTRACT

A process for preparing carboxylic acids by reaction of carbon monoxide with aromatic and aliphatic organic halides, optionally further substituted by groups inert under the reaction conditions, and catalyzed by phosphinic palladium complexes and in the presence of quaternary alkyl-ammonium salts, characterized in that said process is conducted in a double liquid phase consisting essentially of (a) the organic halide and the catalytic palladium complex or their solutions in at least one hydrocarbon solvent immiscible with H₂O, and (b) an aqueous inorganic alkaline solution containing the quaternary alkyl-ammonium salt, at a temperature between about 50° and 150° C. More particularly, the reaction is conducted in the presence of at least one catalyst selected from among:

a. at least one palladium complex of the formula:

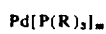

wherein $m$ is a whole number from 2 to 4, and $(R)_3$ represents a homogeneous or a heterogeneous group consisting of phenyl and/or alkyl radicals which may also be further substituted by inert groups;

b. at least one palladium complex of the general formula:

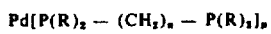

wherein $(R)_3$ has the same meaning indicated above for $(R)_3$, p is a whole number from 1 to 2, and n is a whole number from 1 to 6; or c. at least one palladium complex of the general formula:

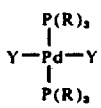

wherein the groups $(R)_3$, equal to or different from each other, have the same meaning as indicated above, and Y is a halogen atom and/or an aryl radical.

8 Claims, No Drawings

PROCESS FOR THE PREPARATION OF CARBOXYLIC ACIDS FROM ORGANIC HALIDES

The present invention relates to a process for the preparation of carboxylic acids starting from organic halides. More particularly, this invention relates to the preparation of carboxylic acids by the reaction of organic halides with carbon nonoxide catalyzed by zero-valent complexes of palladium.

The compounds thus obtained form raw and/or organic intermediate materials having important industrial applications. In fact, they may be used in various technological fields such as for instance in the preparation of cosmetic products (perfumes from benzoic and phenylacetic acids, etc.), products for agriculture (propylamide or 3,5-dichloro-N-(1,1-dimethyl)-2-propenylbenzamide; Cidial, etc.), of dyestuffs and pigments (naphthoic acid), of plasticizers (terephthalic acid), etc.

It is already known to prepare carboxylic acids by the reaction of organic halides with carbon nonoxide, catalyzed by systems based on cobalto- or nickel-tetracarbonyl associated to I and/or Br ions or by iron/manganese systems associated with nickel chloride and thiourea, or by rhodium complexes.

All of these previously known processes, however, show various drawbacks which lie mainly in the preferential use of high pressures of CO, in the necessity to prepare separately the catalyst, and in the reaction rates or in the low yields and in the use of sophisticated solvents.

It is also known to prepare halides of aromatic acids by the reaction of aryl halides with CO in the presence of complex platinum or palladium catalysts. However, this reaction (which is limited to the aromatic halides) is practically conducted under severe temperature and pressure conditions which make the reaction scarcely viable from the industrial point of view. Moreover, since the reaction proceeds in a homogeneous phase, the catalyst must be recovered separately, with consequently a further complication of the process. Lastly, in this latter process, when using aromatic poly-halides, only poly-carboxylated products are possible; that is, it is not possible to progressively substitute the halogens.

The object of the present invention therefore is that of providing a process for the preparation of carboxylic acids starting from organic halides, which shall be free of the above-indicated drawbacks inherent in the prior art processes.

This and still other objects, which will appear more fully to one skilled in the art from the following description, are achieved according to this invention by a process for the preparation of carboxylic acids by the reaction of organic aromatic and aliphatic halides, even substituted by groups inert under the reaction conditions, with carbon oxide, catalyzed by phosphinic complexes of palladium, in the presence of quaternary alkylammonium salts, characterized in that the process is conducted in a double organic/aqueous liquid phase consisting of: (a) the organic halide and the catalytic palladium complex or their solutions in at least one hydrocarbon solvent immiscible with $H_2O$ and (b) an aqueous inorganic alkaline solution containing the quaternary salt, at a temperature between 50° and 150° C.

The starting organic halide may be an organic aromatic or aliphatic chloride, bromide or iodide, as hereinabove defined.

More particularly, the possible substituting groups must be inert under the reaction conditions; thus, for instance, not compatible are carboxylic substituent groups, esterified groups, amidic groups, etc., which obviously would be salified or saponified during the reaction.

The reaction according to this invention, as indicated above, is conducted in an organic/aqueous biphase system consisting, for the organic phase, of organic halide if liquid, or of its solution in a hydrocarbon solvent immiscible with the water in which also the palladium phosphinic catalytic system is soluble; while for the aqueous phase, this consists of an aqueous solution of an inorganic base selected from the class consisting of NaOH and KOH containing the quaternary alkyl-ammonium salt.

The organic hydrocarbon solvent is preferably benzene, toluene, xylene, heptane, etc.

The reaction is conducted at a temperature between 50° and 150° C, and preferably between 80° and 130° C.

The catalyst is a palladium complex with phosphines selected from among:

a. at least a zero-valent palladium complex with $P(R)_3$, i.e., a phosphine of the formula $Pd[P(R)_3]_m$ wherein $m$ is a whole number from 2 to 4 and $(R)_3$ represents a homogeneous or heterogeneous group consisting of phenyl and/or alkyl radicals which, if desired, may preferably be substituted phenyl groups;

b. at least a zero-valent palladium complex of the general formula: $Pd[(R)_2P\text{-}(CH_2)_n\text{-}P(R)_2]_p$ wherein $(R)_2$ has the same meaning as indicated above for $(R)_3$, $p$ is a whole number from 1 to 2, and $n$ is a whole number from 1 to 6; or c. at least one palladium complex of the general formula:

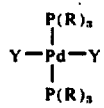

wherein the groups $(R)_3$, equal to or different from each other, have the same meaning as indicated above and where Y is a halogen atom and/or an aryl radical.

The reaction is generally completed in about 2 to 20 hours, depending on the parametric temperature conditions, concentration, type of reactants and catalyst used.

The reaction may schematically be expressed by the following equation:

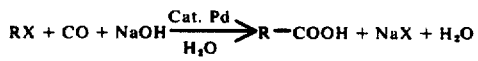

wherein X represents the halogen atom to be substituted and R is the remaining part of the organic halide.

It is possible, starting from organic poly-halides $(R(X)_2, R(X)_3)$, to selectively substitute a halogen atom with the corresponding carboxylic group.

The inorganic base (NaOH or KOH) is introduced as an aqueous solution, preferably in a concentration of around 50% by weight, accompanied by at least one quaternary alkyl-ammonium salt containing a total of at least 6 carbon atoms, such as trimethyl-benzyl-ammonium-chloride, tetrabutyl-ammonium-iodide, etc., into the biphase system of which the organic phase consists of the organic halide, the catalytic palladium complex or their solutions in solvents immiscible in water, for instance saturated aromatic and aliphatic hydrocarbons such as benzene, toluene, heptane, etc.

The concentration of the starting organic halide is preferably between 5% and 20% by weight, the particular values however being in no way critical.

The organic halide may be admixed with the reaction medium slowly.

The molar ratio:base agent/organic halide is preferably greater than equimolar, without however being critical.

As far as the quaternary alkyl-ammonium salts are concerned, their molar ratio with respect to the sodium or potassium hydroxide is not critical. Catalytic quantities will suffice.

The molar ratio between the palladium of the catalyst complex and the organic halide, since it is the case of a catalytic reaction, may vary within wide limits. Convenient results are obtained at any rate with values between 0.1 and 0.0001 for this ratio.

The phosphinic palladium complex catalyst may be accompanied by free phosphines in excess. The phosphinic palladium complex may easily be obtained by reaction of $PdCl_2(C_6H_5CN)_2$ and phosphine directly in the reaction medium, according to techniques well known to the prior art.

A phosphine particularly preferred by reason of its availability and cheapness is the triphenyl-phosphine.

The reaction is finally conducted in a CO atmosphere, preferably at a pressure between atmospheric and about 15 atmospheres.

As starting organic halides may be used, for instance, bromobenzene, dibromobenzene, trichlorobenzene, benzyl chloride, bromostyrene, 1-bromo-naphthalene, iodobutane, etc.

The process, according to one embodiment, may be conducted as follows:

Into a reactor fitted with a stirrer and a temperature regulating device, there were introduced, under a CO atmosphere, the solvent, the caustic, the starting organic halide, and the phosphinic palladium complex catalyst (with possibly also free phosphine) and the quaternary alkyl-ammonium salt.

The organic halide may also be introduced in hydrocarbon solution.

The mixture is then brought up to the desired temperature and is maintained thereat, under a CO atmosphere, until completion of the reaction (i.e., until the end of the absorption of CO).

Thereupon there follow the separation operations of the aqueous phase, operations that may also be conducted in a continuous way, such as by acidifying with concentrated sulphuric or hydrochloric acid and extraction of the acid obtained, according to conventional techniques.

In the meantime, the organic phase may be directly recycled without the need of a separate recovery of the catalyst, owing to the fact that the reaction is biphasic.

The process of the present invention, in comparison with those of the prior art, offers numerous advantages which may be thus summarized:

1. It does not use poisonous metal-carbonyls such as $Ni(CO)_4$ or $[Co(CO)_4]$.
2. The use of the double-phase technique allows a continuous extraction in the aqueous phase of the carboxylic acid from the organic phase, and, thus, an easier execution of a continuous process.
3. The catalyst remains in the organic phase and may be recycled without having to separate it.
4. The presence of the inorganic base and the quaternary alkyl-ammonium salt allows one to operate under milder temperature and pressure conditions in comparison with the prior art.
5. Operating at a low CO pressure (<15 atm) is an essential characteristic of this process for avoiding the formation of substantial quantities of sodium formate, which may easily form at high pressures and temperatures.
6. In the case of the use of poly-halogenated aromatic compounds, this process allows one to obtain the substitution of a single halogen by a COOH group.

The present invention will now be described in the following examples given however merely for illustrative purposes. In Examples 4–7, it is proven (for comparative purposes) that in the absence of NaOH (Example 4) or of quaternary ammonium salt (Example 7), that is outside the conditions of this invention, no carboxylic acid product or at least only one with inferior yields is obtained.

EXAMPLE 1

Into a 50 cc flask fitted with a magnetic stirrer, and under a carbon oxide head, there were introduced bromobenzene (3.0 g), p.xylene (8.0 cc), NaOH at 50% concentration (5.0 cc), tetrabutylammonium iodide (0.2 g), $Pd[P(C_6H_5)_3]_4$ (0.2 g), and triphenylphosphine (0.2 g). The mixture was then brought up to a temperature of 95°–98° C. In about 4 hours and 30 minutes there were absorbed 340 cc of carbon oxide (CO).

The reaction mixture was then diluted with 10 cc of water and transferred into a separator funnel. The aqueous phase was discharged, acidified with concentrated HCl, and then extracted with ethyl ether. The ether extract thus obtained contained 2.0 g of benzoic acid (yield = 86% based on the introduced bromobenzene).

EXAMPLE 2

Into a 50 cc flask fitted with a magnetic stirrer, there were introduced under a carbon oxide head bromobenzene (3.0 g), p.xylene (8.0 cc), NaOH 4N (10 cc), tetrabutylammonium iodide (0.2 g), $Pd[P(C_6H_5)_3]_4$ (0.2 g), and triphenylphosphine (0.2 g). The temperature was raised to 86°–88° C and the mixture was kept under stirring for about 5 hours. There were absorbed 360 cc of CO. The stirring was then interrupted and the two layers were left to separate, whereafter the aqueous solution was syphoned off leaving in the flask the organic phase.

The aqueous phase was then acidified and extracted with ethyl ether. The ether extract was then dried, thereby obtaining 1.7 g of benzoic acid. With the xylene solution were admixed tetrabutylammonium iodide (0.2 g), bromobenzene (3.0 g), NaOH 4N (10 cc), under a CO atmosphere.

The mixture was kept at 86°–88° C, under stirring, for about 12 hours. Thereby were absorbed 380 cc of carbon oxide. The aqueous phase was then separated, acidified and extracted with ethyl ether. The ether extract contained 1.5 g of benzoic acid (yield = 69% based on the total bromobenzene introduced).

EXAMPLE 3

Into a 200 cc autoclave fitted with a magnetic stirrer, a thermometer and a manometer, there were introduced bromobenzene (9.0 g), p.xylene (24 cc), NaOH 4N (30 cc), tetrabutylammonium iodide (0.6 g), triphenylphosphine (0.6 g), and Pd[P($C_6H_5$)$_3$]$_4$ (0.6 g).

The autoclave was then flushed with CO and then pressured to 8 atmospheres of CO. Thereupon the temperature was brought up to 90°–95° C and the mixture kept under stirring at this temperature for about 2 hours and 30 minutes, while maintaining the pressure at 9–10 atmospheres of CO.

The recovery was carried out as in Example 2, thereby obtaining 6.0 g of benzoic acid (with a yield of 85.5% based on the bromobenzene introduced).

EXAMPLE 4

A run conducted in the same way as in Example 3, but without the NaOH did not yield any benzoic acid.

EXAMPLE 5

Into a 100 cc flask fitted with a mechanical stirrer and provided with a thermometer, and under a carbon monoxide head, there were introduced p.dibromobenzene (7.0 g), p.xylene (30 cc), NaOH at 50% (70 cc), $PdCl_2.(C_6H_5CN)_2$ (0.1 g), tetrabutylammonium iodide (0.6 g), and triphenylphosphine (1.2 g).

The temperature was raised to 90° C and the mixture was kept under a CO atmosphere at atmospheric pressure, while stirring vigorously for about 5 hours.

The mixture was processed as in Example 2, obtaining thereby 4.8 of an acid fraction consisting of p-bromobenzoic acid with a titre of 95% (yield = 77% based on the p.dibromobenzene introduced).

EXAMPLE 6

The run of Example 5 was repeated, but using 0.05 g of $PdCl_2.(C_6H_5CN)_2$.

There were obtained similarly 5.2 g of p.dibromobenzoic acid (with a yield of 88% based on the p.dibromobenzene introduced).

EXAMPLE 7

The run of Example 5 was repeated, but without using the tetrabutylammonium iodide.

There were thus obtained 1.5 g of p.bromobenzoic acid. Yield = 25% based on the p.dibromobenzene introduced.

EXAMPLE 8

In the same equipment as was used in Example 5, there were introduced p.dibromobenzene (7.0 g), NaOH at 50% concentration (70 cc), p.xylene (30 cc), $PdCl_2.(C_6H_5CN)_2$ (0.1 g), tetrabutylammonium iodide (0.6 g), and tris(bis-methoxyphenyl)phosphine (1.2 g).

Thereupon the temperature was brought up to 90° C and the mixture kept under stirring for about 4 hours under CO at atmospheric pressure.

The reaction mixture was processed as in Example 2, thereby obtaining 5.1 g of p.bromobenzoic acid at 96% concentration. (Yield = 82% based on the p.dibromobenzene introduced).

EXAMPLE 9

Into a 500 cc autoclave fitted with a mechanical stirrer, there were introduced 1,3,5-trichlorobenzene (7.0 g), p.xylene (50 cc), NaOH at 20% concentration (100 ml), $PdCl_2.(C_6H_5CN)_2$ (0.2 g), triphenylphosphine (0.6 g), and tetrabutylammonium iodide (0.6 g).

After having flushed this mixture with carbon oxide, the autoclave was heated up to 130° C and the mixture maintained at that temperature under stirring and under a pressure of 5–6 atmospheres for about 5 hours.

The aqueous phase was then separated, acidified with hydrochloric acid, and extracted with ethyl ether (3 times with 100 cc). The ether extract, after drying, left a residue of 3.7 g of 3,5-dichlorobenzoic acid.

The xylene solution contained a 1,3,5-trichlorobenzene residue which was recycled.

The yield amounted to 50% based on the 1,3,5-trichlorobenzene introduced.

EXAMPLE 10

Into a 200 cc autoclave fitted with a magnetic stirrer and a thermometer, there were introduced 1,3,5-trichlorobenzene (7.0 g), p.xylene (24 cc), NaOH at 20% concentration (30 cc), $PdCl_2[P(C_6H_5)_3]_2$ (0.6 g), $P(C_6H_5)_3$ (1.2 g), and tetrabutylammonium iodide (0.6 g).

The autoclave was then flushed with carbon oxide, the mixture brought up to a temperature of 110° C and kept at this temperature, under stirring, for about 6 hours under a CO pressure of 9–10 atmospheres. Thereupon the mixture was left to cool down and the aqueous alkaline phase was separated.

To the xylene solution loaded in the autoclave were admixed a 20% NaOH solution (30 cc) and tetrabutylammonium iodide (0.6 g). This mixture was maintained at 110° C for about 6 hours under a CO pressure of 9–10 atmospheres. Thereupon, a second aqueous phase, as indicated above, was separated and then the operation was repeated a third time.

From the three aqueous phases thus obtained were respectively obtained 1.2 g, 1.4 g, and 1.6 g of 3,5-dichlorobenzoic acid.

The yield amounted to 57% based on the 1,3,5-trichlorobenzene introduced.

EXAMPLE 11

Into a 1 liter autoclave fitted with a mechanical stirrer, a thermometer and a submerged fishing inlet tube for the introduction of liquids, there were introduced:

| | |
|---|---|
| p . xylene | 50.0 cc |
| $PdCl_2 . (C_6H_5CN)_2$ | 0.1 g |
| NaOH | 80.0 g |
| $H_2O$ | 200.0 g |
| tetrabutylammonium iodide | 0.6 g |
| triphenylphosphine | 1.2 g |

Thereupon the temperature was brought up to 85°–90° C and, under 5–6 atmospheres of CO, there were introduced in about 3 hours about 25 g of benzyl chloride dissolved in 25 cc of p.xylene. The mixture was maintained at 85°–90° C for about a further 2 hours.

The aqueous phase was then separated, acidified with concentrated HCl and then extracted with ethyl ether (3 times with 100 cc).

The dried ether extract left a residue of 21 g of phenylacetic acid. The yield amounted to 78% based on the benzyl chloride introduced.

EXAMPLE 12

Following the same procedures as described above in Example 1, the following ingredients were combined for reaction: PdCL$_2$.(C$_6$H$_5$CN)$_2$ (33.5 mg), P(C$_6$H$_5$)$_3$ (335 mg), tetrabutylammonium iodide (200 mg), NaOH at 30% concentration (24 cc), p.xylene (10 cc) and p.bromostyrene (2.3 g). The reaction mixture was treated by separating the acid fraction from the neutral fraction by means of sodium bicarbonate. Thereby were obtained 420 mg of cinnamic acid. There was a quantitative yield based on the p.bromostyrene introduced.

EXAMPLE 13

Into a 1 liter autoclave having a mechanical stirrer, a feed pump for liquids, and a thermometer, there were introduced 200 cc of water, 80 g of NaOH, 50 cc of p.xylene, 0.1 g of PdCl$_2$.(C$_6$H$_5$CN)$_2$, 0.3 g of P(C$_6$H$_5$)$_3$, and 0.6 g of tetrabutylammonium iodide.

The internal autoclave temperature was then brought up to 90°–95° C and, under a 6 atmospheres pressure of CO, there were fed in over 4 hours about 25 g of benzyl chloride and 0.3 g of P(C$_6$H$_5$)$_3$ dissolved in 25 cc of p.xylene. There occurs immediately an absorption of Co which is fed in to maintain a pressure of 5–6 atmospheres.

After about a further two hours, the autoclave was discharged and the aqueous phase was separated, acidified, and extracted with ether (3 times with 100 g).

The dry ether left a residue of 20 g of phenyl-acetic acid (with a yield based on the benzyl chloride introduced of 74%).

EXAMPLE 14

Into the same autoclave as in Example 13, there were introduced 200 cc of water, 80 g of NaOH, 50 cc of p.xylene, 0.1 g of PdCL$_2$.(C$_6$H$_5$CN)$_2$, 0.2 g of P(C$_6$H$_5$)$_3$, and 0.6 g of tetrabutylammonium iodide.

Thereupon the autoclave was brought up to a temperature of 95° C and a CO pressure of 5–6 atmospheres and over a period of about 4 hours about 50 g of benzyl chloride and 0.2 g of P(C$_6$H$_5$)$_3$ were fed in. A pressure of 5–6 atmospheres CO was maintained for a total of about 6 hours.

The reaction mass was processed as in Example 13, thereby yielding 45 g of phenylacetic acid. The yield amounted to 83% based on the benzyl chloride introduced.

EXAMPLE 15

Into a 200 cc autoclave fitted with a magnetic stirrer and a thermometer, there were introduced 1-bromonaphthalene (7.3 g), p.xylene (25 cc), NaOH at 25% concentration (30 cc), PdCl$_2$.(C$_6$H$_5$CN)$_2$ (0.2 g), P(C$_6$H$_5$)$_3$ (0.6 g), and tetrabutylammonium iodide (0.6 g).

The autoclave was then flushed with carbon oxide and the internal temperature was brought up to 110° C, at which temperature the above mixture was kept under stirring for about 4 hours under a CO pressure of 9–10 atmospheres. Thereafter the reaction mass was left to cool down and the aqueous alkaline phase was separated, acidified with concentrated HCl, and then extracted with ethyl ether (3 times with about 50 cc).

The dry ether extract left behind 1.9 of a 1-naphthoic acid residue corresponding to a yield of 31% calculated on the bromonaphthalene introduced.

EXAMPLE 16

Into a 200 cc autoclave fitted with a magnetic stirrer and a thermometer, there were introduced 1-iodobutane (4.8 g), p.xylene (25 cc), NaOH at 25% concentration (30 cc), PdCl$_2$.(C$_6$H$_5$CN)$_2$ (0.2 g), P(C$_6$H$_5$)$_3$ (0.6 g), and tetrabutylammonium iodide (0.6 g).

The autoclave was then flushed with carbon oxide and the mixture brought up to a temperature of 110° C, and kept at this temperature under stirring for about 4 hours under a CO pressure of 9–10 atmospheres.

Thereafter the mixture was left to cool down and the aqueous alkaline phase was separated, acidified with concentrated HCl, and extracted with ethyl ether (3 times with 50 cc). The dry ether extract left behind 0.2 g of a residue containing n-valerianic acid.

What is claimed is:

1. A process for the preparation of carboxylic acid by reaction of carbon monoxide with an organic halide selected from the group consisting of aromatic and aliphatic halides, and catalyzed by a phosphine palladium complex selected from the group consisting of (a) a palladium complex of the formula Pd[P(R)$_3$]$_m$ wherein $m$ is a whole number from 2 to 4, and (R)$_3$ represents a homogeneous or heterogeneous group consisting of phenyl and alkyl radicals; (b) a palladium complex of the formula Pd[P(R)$_3$—(CH$_2$)$_n$—P(R$_3$)]$_p$ wherein (R)$_3$ has the same meaning indicated above for (R)$_3$, $p$ is a whole number from 1 to 2, and $m$ is a whole number from 1 to 6; or (c) a palladium complex of the formula

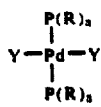

wherein the groups (R)$_3$, equal to or different from each other have the same meaning as indicated above, and Y is a halogen atom and an aryl radical and in the presence of a quaternary alkyl-ammonium salt having a total of at least 6 carbon atoms, characterized in that said process is conducted in a double liquid phase consisting of (a) said organic halide and said catalytic palladium complex or their solutions in a hydrocarbon solvent immiscible with H$_2$O, and (b) an aqueous sodium hydroxide or potassium hydroxide solution containing said quaternary alkyl-ammonium salt at a temperature between about 50° and 150° C, the molar ratio of Pd/organic halide being between 0.1 and 0.0001 and the molar ratio of sodium or potassium hydroxide/organic halide being greater than equimolar, and acidifying the resulting intermediate product to obtain said carboxylic acid.

2. A process according to claim 1, wherein the organic halide is an aromatic chloride, bromide or iodide of benzene, benzyl, styrene or naphthalene.

3. A process according to claim 1, wherein the process is conducted at a temperature between about 80° and 130° C and under a pressure between atmospheric pressure and about 15 atmospheres.

4. A process according to claim 1, wherein the organic phase comprises a solvent selected from the class consisting of benzene, toluene, xylenes and heptane.

5. A process according to claim 1, wherein the aqueous phase consists essentially of an alkaline solution of NaOH or KOH having a concentration of about 50% by weight.

6. A process according to claim 1, wherein the catalyst is complexed to a phosphine.

7. A process according to claim 6, wherein the phosphine is triphenyl-phosphine.

8. The process of claim 1 wherein said organic halide is an organic chloride, bromide or iodide.

* * * * *